United States Patent [19]

Castaldi

[11] Patent Number: 5,232,596
[45] Date of Patent: Aug. 3, 1993

[54] BIO-SLURRY REACTION SYSTEM AND PROCESS FOR HAZARDOUS WASTE TREATMENT

[75] Inventor: Frank J. Castaldi, Austin, Tex.

[73] Assignee: Radian Corporation, Austin, Tex.

[21] Appl. No.: 773,344

[22] Filed: Oct. 7, 1991

[51] Int. Cl.$^5$ .............................................. C02F 3/34
[52] U.S. Cl. ...................................... 210/603; 210/805
[58] Field of Search ............... 423/DIG. 17; 210/602, 210/805, 603, 617, 742, 621, 760, 611

[56] References Cited

U.S. PATENT DOCUMENTS

| | | | |
|---|---|---|---|
| 4,649,117 | 3/1987 | Familletti | 435/313 |
| 4,728,082 | 3/1988 | Emmett et al. | 266/168 |
| 4,729,788 | 3/1988 | Hutchins et al. | 75/118 R |
| 4,732,608 | 3/1988 | Emmett et al. | 75/101 R |
| 5,057,284 | 10/1991 | Emmett, Jr. et al. | 423/DIG. 17 X |

FOREIGN PATENT DOCUMENTS

| | | |
|---|---|---|
| 0197299 | 10/1986 | European Pat. Off. . |
| 0379121 | 7/1990 | European Pat. Off. . |
| 4013552 | 10/1991 | Fed. Rep. of Germany . |
| 8704694 | 8/1987 | PCT Int'l Appl. . |
| 8906992 | 8/1989 | PCT Int'l Appl. . |

*Primary Examiner*—Frank Spear
*Assistant Examiner*—Frank Spear
*Attorney, Agent, or Firm*—Klauber & Jackson

[57] ABSTRACT

A method for improved slurry-phase bioremediation treatment of organic sludge and mixtures of organic sludge and organics-contaminated soils by dissolving the contaminants into an aqueous phase and microbially degrading same. A high solids slurry of the sludge and soils is formed with water and an active bioslurry consisting of large populations of acclimated hydrocarbon-utilizing bacteria and small amounts of biodegradation residue. The slurry is passed through a plurality of in-series bioreactors in each of which a low hydraulic shear is maintained to promote the development of a large population of microorganisms that will form flocculent suspensions. The output from the series of bioreactors is flowed continuously or semicontinuously to a liquid-solids separator to partition the mixed liquor bioslurry from the biodegraded waste residue The mixed liquor bioslurry containing small amounts of biodegradation residue is returned to the slurry being processed for recycling. Off-gas components from the system are recirculated back to one or more of the bioreactors, to return high volatility toxic constituents for increased microbial degradation and control of volatile toxic constituent emissions from the process. The related system is also disclosed and claimed.

17 Claims, 1 Drawing Sheet

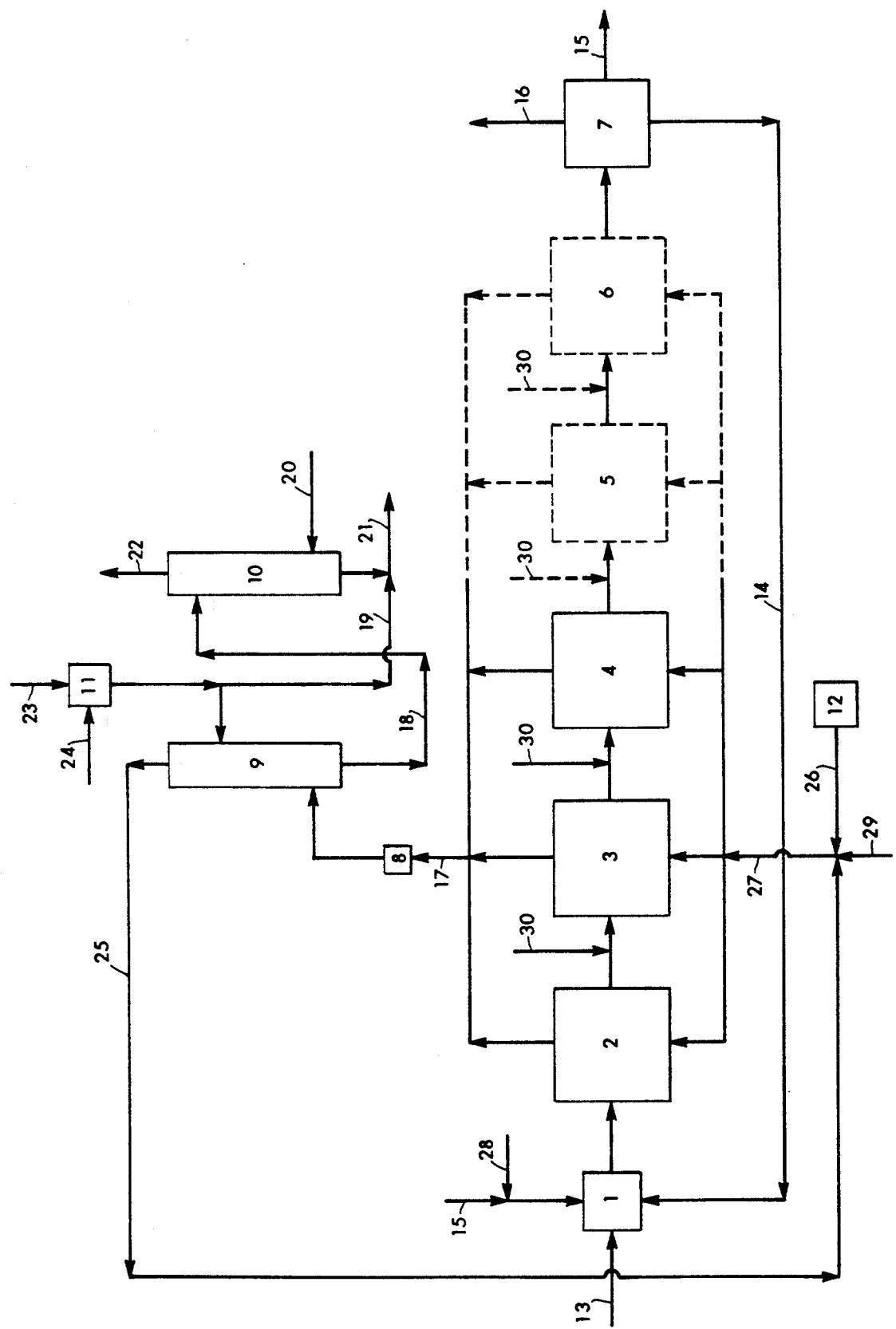

BIO-SLURRY REACTION SYSTEM AND PROCESS FOR HAZARDOUS WASTE TREATMENT

REFERENCE TO DISCLOSURE DOCUMENT

This invention is related to my Disclosure Document No. 239,233, filed on Nov. 13, 1989, which document is hereby incorporated by reference.

FIELD OF THE INVENTION

This invention relates generally to processes and systems for use in the treatment of hazardous wastes; and more specifically relates to a bioremediation method and system for use in the treatment of tarry and oily sludges and associated soils contaminated with microbially degradable organic compounds.

BACKGROUND OF THE INVENTION

The use of bioprocessing to treat waste or waste contaminated material is well-documented. Most refineries in the U.S. have for years been operating land treatment facilities to treat American Petroleum Institute (API) separator sludges, Dissolved Air Flotation (DAF) separator floats, and other petroleum contaminated material. In the U.S., bioprocessing is being utilized to remediate and/or treat several hazardous waste sites contaminated with hydrocarbon material. In the February, 1990 symposium proceedings (EPA—Industry Meeting on Environmental Applications of Biotechnology), the EPA noted that biotechnology has been successfully utilized to treat soils and sludges from 30 to 40 wood preserving sites and that over 200 organic contaminants have been treated successfully using a combination of treatment approaches. Bioprocessing has been used to successfully remediate superfund sites which include contaminants from multiple and varied sources.

Economic and environmental considerations indicate that bioprocessing technologies offer a significant potential for the remediation and treatment of waste and waste contaminated materials. It may be noted in this connection that the areas contaminated with hazardous wastes are usually very large, requiring the treatment of large amounts of solids to meet remediation objectives. The use of ultimate disposal technologies such as incineration or chemical fixation and encapsulation results in very large expenditures of capital, in addition to the liability associated with the handling and transport of these materials to disposal areas. Biodegradation methods entail a lower cost relative to most other approaches because they are conducted on-site and use less complicated equipment. Furthermore, they can be conducted using a combination of above-ground and in situ treatments for a total treatment approach. Biodegradation methods return to the contaminated areas natural microorganisms which, once established, will continue the remediation of the site for years to come. The natural cleansing properties of most waste sites are stimulated by biodegradation methods, which in time benefit those portions of a site which would not normally be treated by alternative approaches (e.g., soils within the vadose zone).

Bioprocessing involves exploiting abilities of indigenous or augmented microorganisms to metabolize organic substrates. This process is beneficial as a remediation option if, through metabolism, the toxic constituents in the contaminated media are converted to nontoxic constituents or their concentration is reduced such that they no longer pose a threat to the human health and environment. Bioprocessing can be accomplished in a land-based environment (e.g., landfarming, composting); it can be performed in tanks (e.g., tank-based groundwater treatment, slurry-phase bioremediation); it can be accomplished in situ by enhancing microbial degradation of contaminants in the subsurface soil; it can be completed under aerobic and/or anaerobic environments; and it can utilize either indigenous or cultured/augmented microorganisms.

Depending upon site specific conditions, processes other than microbial degradation, e.g. volatilization, adsorption, and photodegradation also will take place during bioprocessing. Such physical phenomena tend to put in question the effectiveness of bioprocessing when applied without the use of emission controls and chemical stabilization of treated residues. For the biodegradation process to succeed, at least three criteria must be met. First, a microbial community possessing the appropriate metabolic capacity to effect complex biodegradations must be present. The presence of such a microbial community rests upon prior exposure of these and other naturally occurring microorganisms to similar materials. Second, microorganism-substrate interaction is required, which depends upon the bioavailability of the potential substrate. Finally, environmental parameters such as temperature, pH, availability of oxygen, nutrients and moisture must be conducive to the growth of microorganisms.

A relatively recent bioprocessing approach used to treat contaminated soils and sludges containing certain wood preservatives (e.g., pentachlorophenol), some biodegradable herbicides, and selected hydrocarbon material (e.g., petroleum-based oils and greases) is slurry-phase bioremediation (U.S. EPA Engineering Bulletin—Slurry Biodegradation, EPA/540/2-90/016). This technology is usually a tank-based bioprocessing method that is sometimes referred to as a liquids/solids system. Slurry-phase bioremediation processes treat organic sludges and contaminated soils by extraction and biodegradation. It generally requires extensive, high-power mixing to suspend solids in the slurry-phase and to maximize the mass transfer of the organic contaminants to the aqueous phase where biodegradation normally occurs.

Slurry-phase bioremediation processes generally provide more rapid treatment and require less area than such bioprocesses as landfarms, soil heaps, and compost piles. The residence time in the slurry-phase bioremediation process varies with the waste constituent matrix, physical/chemical properties, contaminant concentration, and constituent biodegradability. Conventional slurry-phase bioremediation processes have the following characteristics:

(a) biodegradation always occurs under aerobic conditions;

(b) batch processing has been the most common mode of operation;

(c) aeration and mixing is generally provided by floating mechanical aerators or high-speed (e.g. 300–800 rpm) mechanical turbines with submerged aeration;

(d) synthetic chemical-based surfactants and dispersants are usually added to achieve waste constituent dissolution; and (e) volatilization rather than biodegradation is typically a major contributor to literature reported waste constituent removals for many contaminant categories (e.g., petroleum aromatics, purgeable halocarbons, polynuclear aromatic hydrocarbons).

Conventional slurry-phase bioremediation processes have decidedly limited waste treatment potential because of the following:

(a) Operation under batch conditions places a small number of unacclimated microorganisms in contact with a waste at its highest pollutional strength. Conventional processes can only compensate by diluting the waste with water and increasing the mixing energy, which increases the amount of aromatic constituent volatilization during treatment.

(b) Addition of synthetic chemical-based surfactants and dispersants often results in microbial inhibition which reduces the biodegradation potential of the process.

(c) The use of floating mechanical aerators and/or high-speed mechanical turbine mixers is very energy intensive, which usually makes operation at high slurry densities (i.e., greater than 25% solids by weight) uneconomical.

(d) The potential for a high degree of waste constituent volatilization suggests the need for air pollution controls on the process. Typical air emission control approaches include vapor phase activated carbon adsorption and/or fumes incineration which adds substantial cost to the process.

SUMMARY OF INVENTION

Now in accordance with the present invention, a method and related system are disclosed, which provide for improved slurry-phase bioremediation treatment of organic sludge and mixtures of organic sludge and organics-contaminated soils by dissolving the contaminants into an aqueous phase and microbially degrading same. A preferred mode of practicing the method includes the steps of:

(a) forming a high solids slurry of the sludge and soils with water and an active bioslurry;

(b) passing the high solids slurry through a plurality of in series bioreactors in each of which a low hydraulic shear is maintained to promote the development of a large population of microorganisms that will form flocculent suspensions;

(c) continuously or semicontinuously flowing the output from the series of bioreactors to a liquid-solids separator to partition the mixed liquor bioslurry from the biodegraded waste residue;

(d) returning the mixed liquor bioslurry containing small amounts of biodegradation residue to the slurry of step (a) for recycling; and (e) recirculating off-gas components from said system back to one or more of said bioreactors, to return high volatility toxic constituents for increased microbial degradation and control of volatile toxic constituent emissions from the process.

The process of the invention uses a combination of hydrocarbon degrading microorganisms, typically in the form of activated sludge from petrochemical treatment bioprocesses and cosubstrates to effect the biodegradation of hazardous constituents in the subject tarry-oily sludges and soils. The approach used involves the addition of large populations of acclimated microorganisms to the hazardous waste material, forming a slurry of waste and microorganisms that is reacted at high mixed liquor concentrations (i.e., 25 to 45% solids of which 70 to 80% is tarry-oily sludge and/or soil, and 20 to 30% is active bioslurry, on a dry weight basis) in stirred tanks to effect either anoxic (i.e., dissolved oxygen concentrations less than 0.5 mg/L) or aerobic (i.e., dissolved oxygen concentrations greater than 2.0 mg/L) degradation of the pollutants at temperatures optimal for microbial growth and substrate utilization. This approach to biodegradation is predicated on providing a sufficient inventory of acclimated microorganisms to achieve the full potential of the bioremediation process.

The mechanism for either oxidative (i.e., aerobic) or reductive (i.e., anaerobic) biodegradation of hazardous wastes is an initial dissolution of the waste constituents into the aqueous-phase followed by actual biodegradation of the constituents through normal metabolisms of facultative anaerobic microorganisms. The dissolution of waste constituents results from the formation of microbial surfactants that act as emulsifiers dispersing the more oleophilic constituents into the aqueous-phase. The addition of a cosubstrate (such as toluene) to the mixed liquor enhances the biodegradation of certain waste constituents through the mechanism of cometabolism, providing the microorganisms with an additional carbon source for biosynthesis. Waste constituent biodegradation is a synergistic cometabolic phenomenon, where the diverse physiologies of numerous microorganisms cultured on an alternative carbon source act together to successively attack, transform, and degrade complex organic molecules such as phenolics and polynuclear aromatic hydrocarbons (PAHs). Under anoxic conditions, a reductive biodegradation occurs which results in dehalogenation of certain purgeable halocarbons and some polychlorinated biphenyls. This process also proceeds in the presence of a selected cosubstrate which provides a carbon source to the microbes for both energy and biosynthesis. When returned to an aerobic metabolism, the facultative anaerobic microbes complete the degradations of low molecular weight halogenated constituents to carbon dioxide, water, and a halide.

Pursuant to the process of the invention, a continuous or semicontinuous feed is maintained to a series of stirred tank reactors (i.e., approaching a plug flow condition), initially providing a high ratio of substrate concentration to microorganism population, then tapering the load through the reactor system in the same manner as a batch decay reaction. Bioslurry is recirculated to control the substrate to microorganism ratio of the process during continuous or semicontinuous treatment and provide a renewable process much in the same manner as conventional activated sludge treatment of liquid wastes. High oxygen transfer efficiencies in deep tank reactors are maintained during aerobic treatment while utilizing a low hydraulic shear environment to promote the development of a large population of facultative anaerobic microorganisms that form the flocculent suspensions necessary to attain a biomass separation after treatment. Off-gas recirculation is used to collect and return volatile hydrocarbons to the reactor system for enhanced treatment. The purgeable aromatics and halocarbons are biodegraded in a continuous gaseous throughput system where the residence time in contact with the microbes is greater than the minimum allowable kinetic rate of decomposition for the compound of interest.

Alternating anoxic and aerobic stirred tank reactors may be used to effect a combination reductive and oxidative dehalogenation of chlorinated hydrocarbons in the wastes to improve biodegradation of purgeable halocarbons and some polychlorinated biphenyls (PCBs) and other halogenated organics. In this process, the chlorinated isomers of PCB above pentachlorobiphenyl are dehalogenated under anoxic conditions, while some lower molecular weight chlorinated isomers are degraded by an oxidative metabolism. Chlorinated isomers of PCB with molecular weight greater than pentachlorobiphenyl appear to be persistent in this process when operated under strict aerobic conditions.

The addition of selected cosubstrates to the waste/microorganism mixture provides a readily biodegradable carbon source to effect improved treatment of complex halogenated and non-halogenated hydrocarbons. These cosubstrates may be present in the waste material (e.g., toluene in petroleum wastes) and their use can be optimized through the addition of active bioslurry recirculation and/or off-gas recirculation of readily biodegradable purgeable aromatics (under both aerobic or anoxic conditions). Suitable cosubstrates include the purgeable aromatics toluene and para-xylene; phenolics such as simple phenol and para-cresol (i.e., 4-methyl-phenol); phenyldecane; hexadecane; para-naphthalic acid (i.e., benzene paradicarboxylic acid); biphenyl; benzoate; camphor; pyrene; and butanone (i.e., ethyl methyl ketone). These compounds are effective cosubstrates because they are more hydrophilic than the pollutants of interest, induce cytochrome oxidase production in facultative anaerobic microorganisms, provide the nucleus of some higher molecular weight pollutants (e.g., Benzo(a) anthracene), and can act as growth substrates (i.e., support growth of microorganisms).

The bioremediation system and process of the invention is generally useful in the treatment of tarry and oily sludges and associated soils contaminated with one or more of the following groups of compounds: (1) Purgeable aromatics (e.g. benzene, toluene, xylenes, ethylbenzene, and styrene); (2) purgeable halocarbons (e.g., chlorobenzene, 1,2-dichlorobenzene, 1,2-dichloroethane, and trichloroethylene); (3) polynuclear aromatic hydrocarbons (e.g., naphthalene, pyrene, acenaphthene, anthracene, and chrysene); and (4) polychlorinated biphenyls with chlorinated isomers below pentachlorobiphenyl. The pollutants in tarry and oily sludges and associated soils are treatable by the subject bioremediation system to several hundred milligrams of constituent per kilogram of waste material at ambient or higher temperatures.

The microbial-based hazardous waste treatment process can be successfully applied to the treatment of the numerous hazardous wastes and associated liquids including: refinery and petrochemical production oily sludges and asphaltic-type wastes; process waste slurries from organic chemicals production (e.g., styrene tars, solvent contaminated sludges from process tank bottoms); wood-tar based creosote (i.e., phenols and phenol derivatives) contaminated sludges and possibly coal-tar based creosote (i.e., naphthalene and anthracene) contaminated sludges; some PCB contaminated sludges and soils from CERCLA sites; and fuel oil and diesel fuel contaminated soils from spill areas.

BRIEF DESCRIPTION OF THE DRAWING

In the drawing appended hereto:

The Figure is a schematic block diagram of a system operating in accordance with the invention.

DESCRIPTION OF THE PREFERRED EMBODIMENT

The present invention may utilize a generally conventional bioreactor which can be modified to improve volatile hydrocarbon biodegradation, to better control volatile organic compound (VOC) emissions, and to improve system waste load treatment potential. A reactor system in accordance with the invention appears in this Figure. This system includes four main components: a waste dissolution section, the bioreactor train section, a liquid-solids separation section, and an off-gas management section.

Waste 13, typically in the form of a tarry, oily sludge and soil mixture, is fed into the first stage waste dissolution reactor 1 where solids are kept suspended by a radial flow turbine mixer. Decant water and bioslurry from the liquid-solids separation section 7, and makeup water, are provided respectively at 15, 14, and 28. If volatilization of toxic organics represents a potential problem, the waste dissolution reactor is covered, and connected to the off-gas management system used also for the aerobic bioreactors. Rotary positive displacement pumps which utilize flexible parts (not shown) are used to pump feed sludge to the waste dissolution reactor 1. The flexible member pump operates continuously and feed may be recirculated back to the feed tank (not shown) for most of the time. A timer is used to actuate flow during pre-set intervals to the first stage waste dissolution reactor 1. Nutrients may either be added to the feed in the waste dissolution reactor or directly to any or all of the downstream process bioreactors. The selected points of nutrient addition to the process depends on the amount of bioemulsification required to achieve the organic treatment objectives. The feed can be pre-heated by running it through an optional heat exchanger (not shown). Heat may also be derived from the gas compressor cooling water system used by a centrifugal displacement type vacuum pump which can handle a mixture of air and water (not shown).

In accordance with the invention, the waste to be degraded passes through a series of in-line slurry bioreactors, schematically depicted as being up to five in number—i.e., reactors 2, 3, 4, 5 and 6. Preferably at least three aerobic bioreactor stages are used—shown herein as reactors 2, 3, and 4, with the two further optional stages 5 and 6 being shown in shadow. Each reactor is of the complete mixed type. The more stages that are used the closer the biodegradation kinetics will approach those of an ideal plug flow reactor. Because bioflocculation is a first order reaction with respect to total microorganism number, the process is designed to exhibit a residence time distribution approximating plug flow. The tarry, oily waste materials treated by the process must be well mixed to achieve optimum biokinetics for substrate decay and microbial growth. Therefore, a combination of continuous-stirred tank reactors in series is the most appropriate process configuration.

Bioreactors which are most appropriate for use with the process are stirred tanks with radial or longitudinal stirrers; stirred tanks with aspiring turbines; stirred tanks with draft tube aerators; deep jet reactors; and airlift reactors with internal or external airlifts. To prevent the formation of surface float and the accumulation of bottom sediment as well as to obtain a thorough mixing of the contents of the reactor, thereby ensuring the mixing-in of the newly added waste, any or all of the following methods may be used in the reactors:

stirring by applying gas via diffusers into the slurry mass;

revolution through stirring or mixing devices, such as axial or radial flow turbines;

revolution through airlift or draft tube displacement systems internal to the reactor; and revolution through pumps arranged outside the reactor.

The bioreactors are designed to both enhance the dissolution of tars and heavy oils into the aqueous phase and achieve optimal conditions for microbial degradation of the tars and oils. To this end, bacterial growth limitations must be prevented and biooxidation of organics must exist everywhere in the reactor. The prevention of bacterial growth limitations requires a stirred tank reactor to adequately distribute nutrients and dissolved oxygen to the microorganisms. Optimal biodegradation of organics occurs under plug flow conditions. Therefore, a system configuration which combines the two reactor types will achieve both objectives. This is satisfied by the use of continuous stirred tank reactors in a series configuration.

A third condition of reactor design for the process is that the bioreactor promote bioflocculation. Because stirred tank reactors typically experience highly turbulent flow conditions, biofloc breakup often occurs. Small floc particles are sheared from larger aggregates when the local shear stress exceeds the internal binding forces of the aggregate. In a highly turbulent environment, biofloc breakup results from surface erosion and floc splitting.

Those schooled in the art know that the rate of aggregate breakup is proportional to power input to the bioreactor. As the viscosity of a tarry, oily slurry increases, power input needed to affect mixing will also increase. Increased power consumption will result in intense shear fields in the reactor which can damage the microorganisms in the process. Ultimately, all energy introduced in the reactor will be transformed into heat, thus leading to an increase of cooling requirements in addition to higher power costs.

Because of their simple construction and economical mixing characteristics, airlift loop reactors were employed within the process as reactors 2, 3, 4, 5, and 6. These slurry bioreactors are generally conventional—representative devices of this type are shown in U.S. Pat. Nos. 4,728,082, 4,729,788, 4,649,117, and 4,732,608. Airlift loop reactor performance is sufficiently versatile to prompt its use in biological acid leaching processes and industrial fermentations. Owing to the diffuse nature of the power dissipation through the expansion of a sparging gas, airlift loop reactors afford excellent agitation of a slurry with minimum mechanical shear. The design provides gentle agitation without the need to employ mechanical mixing which might damage shear-sensitive microbial cultures. Airlift loop reactors also are effective for mixing non-Newtonian fluids such as the tarry, oil slurries typical of this invention.

The airlift loop reactor consists of two chambers, interconnected at top and bottom. In one chamber, the riser, gas is sparged at the bottom. The gas rises and escapes at the top. Therefore, under most circumstances there is no gas present in the other chamber, the downcomer. The density difference between riser and downcomer causes an intensive liquid circulation. Typically, two airlift designs are used—the internal and the external loop reactors. The aforementioned U.S. patents are examples of internal airlift loop reactors.

The liquid mixing times for airlift loop reactors are known to decrease with increases in gas sparging rate. It also is known that aeration results in a decrease in the power number for stirred tank reactors caused by a decrease in pumping capacity due to cavity formation. This is one of the reasons that the mixing time increases in stirred tank reactors when sparged aeration is used to provide dissolved oxygen to a microbial slurry. Hence, airlift loop reactors show a definite advantage over stirred tank reactors at high superficial gas flow rates.

Airlift loop reactors typically operate in the flow regime known as bubble flow. This suggests that plug flow prevails in airlift risers. However, no measurements of local flow phenomena have been reported in the literature to substantiate this assumption. When the downcomer section volume of an airlift loop reactor is increased in size many times that of the riser section and a gently diffused gas is introduced into the bottom of the downcomer, an agitated condition develops in the downcomer section which approaches that of an ideal stirred tank reactor. When a plurality of fine bubble diffusers are used to introduce the gas, the characteristic gentle agitation condition of an airlift loop reactor is still maintained. However, the downcomer will now be capable of mixing a slurry of moderate density. This is, in part, the apparatus as applied to microbial mineral recovery described in U.S. Pat. Nos. 4,728,082 and 4,732,608. The present invention maintains that highly viscous slurries of tarry, oily residues from petroleum and petrochemical operations can be best mixed in such a reactor when a low-speed axial flow turbine also is installed with the airlift. The preferred conditions are that the downcomer be a minimum of a thousand times the cross-sectional area of the riser, and that the diffused gas stream within the downcomer produce bubbles of 4.5 millimeters or less to prevent aggregation of the bubbles into larger masses. The axial flow turbine within the downcomer is designed to induce fluid motion down toward the center of the reactor and then upward in the direction of the flow of diffused gas. The preferred design is to have a complete revolution of reactor content every 15 to 30 minutes. This condition will both minimize energy consumption for mixing and enhance the potential for bioflocculation of bacteria in later reaction stages of the process.

The bottoms of the process bioreactors when treating tarry, oily residues from petroleum-petrochemical wastes are primarily composed of asphaltic emulsions of high viscosity. The typical kinematic viscosity ranges for these asphaltic emulsions are between 1000 and 7000 Seconds Saybolt Universal (SSU) units. These emulsions must be resuspended into the reaction zone of the process bioreactor if microbial treatment is to be effective. It is an aspect of this invention that resuspension of asphaltic emulsions is accomplished through the use of rotary positive displacement pumps of the following types: axial flow screw pumps, internal gear pumps, internal lobe pumps, flexible liner pumps, and flexible tube pumps. Of these, single-screw and flexible tube pumps are preferred. The range of typical process reactor volumetric turnovers that result from the use of these pumps is between 1.0 and 1.5 times per hour. In the waste dissolution reactor 1, it is preferable to utilize a low-speed radial flow turbine, which provides relatively high shear at low mixing speeds, generally in the range of 20 to 50 rpm. This induces high level mixing for enhanced waste dissolution when in the presence of large populations of acclimated microorganisms.

All bioreactors are arranged in a cascading mode and operated at varied mixed liquor levels. The reactors are completely gas-sealed. The first stage waste dissolution reactor 1 is preferably operated under anoxic conditions to induce an anaerobic microbial metabolism at this section. The objective of the operation occurring at the first stage 1 is to form a stable emulsion, basically one of water-in-oil, i.e., typically an emulsion in tar. The wastes here are heavy residuals which are very viscous, usually from 3000 to 10,000 centipoises of absolute viscosity. It is desired to render these materials less viscous in order to facilitate their breakdown by the microorganisms. The long-chain hydrocarbons in the wastes are essentially water-insoluble compounds. Unlike water-soluble growth substrates, which maintain constant contact with the microorganisms, water-insoluble substrates must be transported to the bacterial cell in some way so as to achieve microbe-substrate contact. It is an aspect of this process that long-chain hydrocarbons are solubilized using biochemical mechanisms such that hydrocarbon droplets less than 1 $\mu m$ in diameter are dispersed throughout the aqueous medium. This is accomplished through the presence of extracellular hydrocarbon-emulsifying and -solubilizing agents produced by hydrocarbon-utilizing bacteria within the bioreactors. By providing an anoxic environment, one assures the presence of appropriate enzymes that enhance production of biosolvents and biosurfactants that act to induce waste constituent dissolution during treatment. The majority of the biosurfactants are probably extracellular such that they aid the emulsification of hydrocarbon waste material. Some may also exist within the cell walls and probably assist in transport of hydrocarbons into the microbe. Typical biosurfactants are glycolipids and amino acid lipids. The classification of the biosurfactant is determined by the microorganism responsible for its production. Under the anoxic conditions the facultative anaerobic microorganisms will switch from their normal respiratory mode of oxidative phosphorylation to a fermentation metabolism. In order to assure the absence of air, mixing in the initial stage is carefully controlled so that no vortices are formed, i.e., to avoid drawing of air into the liquid.

Under nutritional conditions which support balanced aerobic growth facultative anaerobic bacteria will metabolize the substrates into new cell material and carbon dioxide. There is very little production of partially oxidized carbon compounds or extracellular polysaccharides. However, under unbalanced aerobic growth conditions (i.e., some components of the bacteria are not provided at a concentration that supports cell duplication), the facultative anaerobic bacteria will produce relatively large amounts of polysaccharides and biosurfactants which are useful in the process. The critical amounts of nutrients are commonly taken as Biochemical Oxygen Demand (BOD):Ammonia-Nitrogen ($NH_3$—N) and BOD:$PO_4$—P ratios of 20:1 and 100:1, respectively. The available form of phosphate-phosphorus ($PO_4$—P) is provided to the bacteria as orthophosphate ($PO_4^{3-}$, $HPO_4^{2-}$, $H_2PO_4^{-}$). It is a condition of the invention to increase one or both of these ratios to induce the production of extracellular polysaccharides and biosurfactants.

Under unbalanced anoxic growth conditions, the same facultative anaerobic bacteria produce relatively large amounts of biosolvents such as alcohols and organic acids. Typical biosolvents produced under this condition are butanol, acetic acid, and butyric acid. The production of biosolvents during anoxic growth of the facultative anaerobic bacteria reduce the interfacial and surface tension forces of the slurry, thus releasing oil from the tarry waste.

Biosolvent production will also occur in the aerobic second stage bioreactor z when this reactor is operated at a dissolved oxygen concentration below 2.0 mg/L. Below the limiting oxygen concentration, the second stage bioreactor z behaves as an anoxic reactor. Consequently, a portion of the microorganism population within the bioslurry exists under a fermentation mode of metabolism.

The presence of two bacterial genera define the microbiology of the process: genus Pseudomonas in the family Pseudomonadaceae and genus Acinetobacter in the family Neisseriaceae. In general, these bacterial genera are characterized by gram-negative aerobic rods and cocci. These genera were identified in isolates from process reactor seed sludge (Table I).

TABLE I

| Microbes Isolated from Reactor Seed Sludge | | |
|---|---|---|
| Test | Microorganism | |
| Biolog ID | Acinetobacter johnson II | Acinetobacter lwoffi |
| Gram Reaction | − | − |
| Morphology | Pairs of Rods | Clusters of short rods approaching coccus shape |
| Pigment | Cream | Cream |
| Catalase | + | + |
| Oxidase | − | − |
| Motility | $-^a$ | $-^a$ |
| Indole | − | − |
| Ornithine | + | + |
| Biolog ID | Pseudomonas sp.$^b$ | Pseudomonas fulva |
| Gram Reaction | − | − |
| Morphology | Rods | Clusters of rods |
| Pigment | White | Cream |
| Catalase | + | + |
| Oxidase | + | + |
| Motility | + | + |
| Indole | − | − |
| Ornithine | + | + |

$^a$Cells display twitching motility presumably because of the presence of polar fimbriae.
$^b$Species not identified.

The pseudomonads are one of the largest groups of aerobic, chemoheterotrophic bacteria. They are capable of using numerous organic compounds as sole sources of carbon and energy. These microbes are metabolically versatile free-living bacteria which occur in soil and water. The metabolism of Pseudomonas is typically respiratory with oxygen as the terminal electron acceptor, but many species can also use nitrate as an alternate electron acceptor under anaerobic conditions. Some cytochromes are involved in denitrification through the participation of a special cytochrome oxidase.

Many aromatic compounds can be used for growth by Pseudomonas species. A number of these compounds (e.g., benzoate, p-hydroxybenzoate, tryptophan, phthalate) may be metabolized by pseudomonads following pathways that converge to a common intermediate, β-ketoadipate. This intermediate is formed soon after the last aromatic compound is cleaved through enzymatic action (N. J. Palleroni, *The Pseudomonas Group*, Meadowfield Press, Shildon Co., Durham, England). This is commonly known as the β-ketoadipate pathway. Most aerobic bacteria that use aromatic compounds as respiratory substrates attack them through one or other of the two convergent branches of the β-ketoadipate pathway.

Two pseudomonads isolated from the process reactors are characterized by their nutritional requirements in Table II. It is generally accepted that both short- and long-chain alkanes are monoterminally oxidized to the corresponding alcohol, aldehyde, and monobasic fatty acid by these and other Pseudomonas species. These pseudomonads can also utilize unsubstituted alicyclic hydrocarbons (e.g., cyclohexane). Common metabolic intermediates include cyclohexanol, adipic, formic, and valeric acids. In addition to the suggested intermediates of cyclohexane catabolism, Pseudomonas aeruginosa can grow on n-hexadecane, benzene, cyclohexeneoxide, and methylcyclohexane (J. Gen. Microbiol. 120:89–94). Therefore, the pseudomonads may be capable of growth on both normal paraffins and cycloparaffins.

TABLE II

| Microbes Isolated from Process Reactors | | |
|---|---|---|
| Test | Microorganism | |
| Biolog ID | *Pseudomonas aeruginosa* | *Pseudomonas azelaica* |
| Gram Reaction | − | − |
| Morphology | Long Rods | Long Rods |
| Pigment | Cream | Cream |
| Catalase | + | + |
| Utilizes: | | |
| Cyclodextrin | − | − |
| Dextrin | − | − |
| Glycogen | − | − |
| Tween 40 | + | + |
| Tween 80 | + | + |
| N-acetyl-D-galactosamine | − | − |
| N-acetyl-D-glucosamine | + | − |
| Adonitol | − | − |
| L-arabinose | − | − |
| D-arabitol | − | − |
| Cellobiose | − | − |
| I-erythritol | − | − |
| D-fructose | + | − |
| L-frucose | + | + |
| D-galactose | + | − |
| Gentiobiose | − | − |
| D-glucose | + | + |
| M-inositol | − | − |
| Lactose | − | − |
| Lactulose | − | − |
| Maltose | − | − |
| D-mannitol | + | − |
| D-mannose | + | − |
| D-melibiose | − | − |
| Methyl glucoside | − | − |
| Psicose | − | − |
| D-raffinose | − | − |
| L-rhamnose | + | + |
| D-sorbitol | − | − |
| Sucrose | − | − |
| D-trehalose | − | − |
| Turanose | − | − |
| Xylitol | − | − |
| Methyl pyruvate | + | + |
| Mono-methyl succinate | + | + |
| Acetic acid | + | + |
| Cis-aconitic acid | + | + |
| Citric acid | + | + |
| Formic acid | − | + |
| D-galactic acid lactone | − | − |
| D-galacturonic acid | − | − |
| D-gluconic acid | + | + |
| D-glucosaminic acid | − | − |
| D-glucuronic acid | − | − |
| A-hydroxybutyric acid | − | + |
| B-hydroxybutyric acid | + | + |

TABLE II-continued

| Microbes Isolated from Process Reactors | | |
|---|---|---|
| Test | Microorganism | |
| G-hydroxybutyric acid | − | − |
| P-hydroxyphenylacetic acid | + | − |
| Itaconic acid | + | − |
| Ketobutyric acid | − | + |
| Ketoglutamic acid | + | + |
| Ketovaleric acid | − | + |
| D,L-lactic acid | + | + |
| Malonic acid | + | − |
| Propionic acid | + | + |
| Quinic acid | + | − |
| D-saccharic acid | − | − |
| Sebacic acid | − | + |
| Succinic acid | + | + |
| Bromosuccinic acid | + | + |
| Succinamic acid | + | − |
| Glucuronamide | − | − |
| Alaninimide | − | − |
| D-alanine | + | + |
| L-alanine | + | + |
| L-alanyl-glycine | − | + |
| L-asparagine | + | + |
| L-aspartic acid | + | + |
| L-glutamic acid | + | + |
| Glycl-L-aspartic acid | − | − |
| Glycl-L-glutamic acid | − | − |
| L-histidine | + | − |
| Hydroxy L-proline | − | + |
| L-leucine | − | + |
| L-ornithine | + | + |
| L-phenylalanine | − | − |
| L-proline | + | + |
| L-pyroglutamic acid | + | − |
| D-serine | − | − |
| L-serine | − | + |
| L-threonine | − | + |
| D,L-carnitine | − | + |
| Amino butyric acid | + | + |
| Urocanic acid | + | + |
| Inosine | + | + |
| Uridine | − | − |
| Thymidine | − | − |
| Phenylethylamine | − | − |
| Putrescine | + | + |
| 2-amino ethanol | + | + |
| 2,3-butanediol | − | − |
| Glycerol | + | − |
| D,L-glycerol phosphate | − | − |
| Glucose-1-phosphate | + | − |
| Glucose-6-phosphate | + | − |

Microorganisms of the genus Acinetobacter were also isolated from the process reactor seed sludge (Table I). These bacteria are common members of the microflora of soil and water. They do not require growth factors (i.e., additional organic compounds for cell synthesis) and are nutritionally versatile, able to utilize a range of organic substrates almost as extens've as the range used by pseudomonads. It is commonly known that Acinetobacter species play a role analogous to the pseudomonads in the degradation of organic wastes and can be enriched by similar techniques. Among the organic compounds degraded are hydrocarbons (e.g., n-hexadecane), aromatic compounds such as benzoate or quinate, and alicyclic compounds such as cyclohexanol (Eur. J. Biochem 60:1–7). Since all acinetobacters are oxidase-negative, they lack cytochrome c. However, they do contain cytochromes of the a and b variety. Acinetobacters also contain all the enzymes of the tricarboxylic acid cycle as well as those of the glyoxylate cycle. Many Acinetobacter species are capable of growth on long-chain alkanes ($C_{10}$–$C_{20}$), alkenes, certain branched-chain alkanes, most primary alcohols, α, -diols, long-chain aldehydes, mono- and dibasic fatty acids, and a variety of other substrates (R. M. Atlas, *Petroleum Microbiology*, Macmillan Publishing Company, USA).

It is a further aspect of this process that these genera of hydrocarbon-utilizing bacteria are also capable of producing extracellular long-chain hydrocarbon-emulsifying and -solubilizing agents. These agents are extracellular rhamnolipids, a form of glycolipid composed of rhamnose and β-hydroxydecanoic acid; ornithine-containing lipids; and amphipathic (i.e., having both hydrophilic and hydrophobic groups) polysaccharide bioemulsifiers. The rhamnolipids are produced by several strains of *Pseudomonas aeruginosa* and work by decreasing the aqueous surface tension and lowering interfacial tension between oil and water. These same microorganisms are also capable of producing amino acid-containing lipids such as a peptidoglycolipid composed of over 50 amino acid residues, a lipid moiety of 11 fatty acids, and a sugar moiety (Mikrobiologiya 52(5):767).

Several of the hydrocarbon-utilizing bacteria genus Acinetobacter are capable of producing lipoheteropolysaccharide-type molecules. The amphipathic polysaccharide bioemulsifiers usually have a strong affinity for oil-water interfaces. Polysaccharide emulsifiers usually do not lower interfacial tension. However, their preference for the interface makes them very effective emulsion stabilizers. Although the high molecular weight extracellular bioemulsifiers are not particularly effective in reducing interfacial tension, they do have the property of binding tightly to an interface and apparently stabilizing the emulsion and preventing droplet coalescence.

Additives may be provided particularly to the reactor downstream of the first stage to contribute to the stability of the emulsion and to effect density differences between the waste and microorganism mass, thereby facilitating separation and formation of flocculating microbe particles. Among such additives are adsorbing clays such as bentonites or attapulgites.

At the third stage 3 air also is introduced. Dissolution is still continuing to occur due to biosurfactant production concomitant with biodegradation. However, mixing is intentionally less agitated. At this and subsequent stages, as indicated, an axial flow turbine is used with a low speed between 30 and 50 rpm so as to assure relatively low aggregate shear rates and reduced turbulence. It is a further aspect of the invention that a decreased level of agitation results in an increase in biosurfactant production.

The gas space above each process reactor containing a mixture of primarily nitrogen, oxygen, carbon dioxide, and any volatilized organics, is evacuated and recompressed using a centrifugal displacement type vacuum pump which can handle a mixture of air and water. It is subsequently analyzed for its oxygen and carbon dioxide content by two in-line gas analyzers. Oxygen concentration in the gas stream is maintained by injecting pure oxygen 26 into the system from an oxygen plant 12. Carbon dioxide which is a metabolic end product of the biodegradation process is adjusted by directing the gas stream, when indicated, through a $CO_2$ removal reactor or absorber 9. This is a packed bed absorption tower filled with ceramic or steel turnings. The process has the requirement to remove carbon dioxide from the recirculating off-gas without also removing volatile waste constituents as well. To achieve this requirement, a concentrated solution of sodium or potassium carbonate at between 25 and 35 weight percent in water is circulated between the $CO_2$ removal reactor (absorber) 9 and the scrubber solution regeneration reactor (stripper) 10. The carbon dioxide is absorbed via an acid-base reaction mechanism as follows:

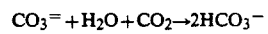

$$CO_3^= + H_2O + CO_2 \rightarrow 2HCO_3^-$$

Hydrocarbons are generally very insoluble in such a high ionic strength solution.

As shown in the Figure, the carbon dioxide removal aspect of the present invention consists of an absorber 9 for removal of $CO_2$ from the process off-gas and an air stripper 10 to regenerate the $CO_2$-rich recirculating (scrubber) solution 18. The carbon dioxide-bearing gases 17 at ambient temperature, after passing through the vacuum vent regulator 8, enter the absorber 9 and are passed countercurrent to the carbonate solution ($CO_2$-lean scrubber solution) 19. The amount of carbon dioxide absorbed in this solution varies with temperature, pressure, partial pressure of carbon dioxide in the off-gas, and solution strength. The process operates at what is essentially atmospheric pressure and ambient temperatures between 20° and 35° C. The partial pressure of carbon dioxide in the process off-gas will generally vary between 4 and 6 percent by volume. Target $CO_2$-lean recycle gas 25 carbon dioxide partial pressures are between 0.5 and 1.0 percent by volume. The preferred scrubber solution is potassium carbonate at 30 weight percent in water because it is more soluble than the corresponding sodium salt and permits a more efficient absorption than equivalent solutions of sodium carbonate.

The $CO_2$-rich scrubber solution 18 is regenerated by stripping the solution with air 20 at ambient temperatures between 24° and 30° C. The $CO_2$-rich exhaust air 22 is liberated to the atmosphere, and a $CO_2$-lean scrubber solution 19 is returned to the absorber for reuse. The stripper also is a packed bed tower filled with ceramic or steel turnings. Periodic blowdowns of scrubber solution 21 are required to adjust the ionic strength of the carbonate solution, while fresh scrubber reagent 23 is blended with water 24 to provide makeup scrubber solution 11 to the process.

After the waste is processed through the series of bioreactors 1-6, a liquid-solids separation device 7 is used for separation of mixed liquor bioslurry 14 and liquid decant 15 from the biodegradation residue 16. The mixed liquor bioslurry 14 which may contain small amounts of biodegradation residue is returned via a bioslurry return line to the head of the reactor train for contact with raw waste material in the first reactor of the train. The biodegradation residue is collected in a hopper or trough inside the liquid-solids separator. Biodegradation residue is sent to a treated waste landfill after possible additional processing for heavy metal recovery or stabilization and solidification, and decant liquid 15 is sent to wastewater treatment.

The liquid-solids separation device is used for partitioning of the mixed liquor bioslurry from the biodegraded waste residue. The process may either employ a conventional gravity separator with a plow scraper-type sludge collector or a microscreening device. The type of liquid-solids separation device used with the treatment system depends on the nature of the biodegraded waste residue produced. Heavy viscous sludges are best separated in either thickener-clarifier devices with staggered plows that progressively move the sludge towards a central hopper or flotation-thickeners.

The design of the liquid-solids separator is such that three distinct layers can be observed: (1) a biodegraded waste residue layer; (2) a mixed liquor bioslurry layer; and (3) a liquid decant layer. These three layers are withdrawn separately and either pumped back to the head of the process or stored separately for final processing and/or ultimate disposal.

The biodegraded waste residue is distinguished from the mixed liquor bioslurry by color (grayish-black vs. chestnut-brown); texture (gelatinous sludge vs. flocculent liquid-solid suspension); and density (specific gravity 1.1 to 1.4 vs. 0.98 to 1.02). The decant layer is a grayish-black liquid with a polished appearance, generally at lower levels relative to the waste of suspended solids and chemical oxygen demand.

Gas to the airlift and the diffusers may be supplied separately through rotary valves, located on the reactor top. The respective gas flows are metered through rotameters. The reactors may be insulated to minimize heat loss. Typically they are run at a mixed liquor temperature between 25°-35° C., with 35° C. being optimal for growth and biodegradation kinetics. At lower temperatures, a heat exchanger may be used to preheat the waste feed. A slight vacuum is maintained in all reactors to prevent the loss of volatile hydrocarbon material from the process. The mixed liquor leaves the final reactor through a barometric leg in the liquid-solids separator to maintain the gas seal.

Coalescing filters are used on the gas lines leading to the gas analyzers in order to avoid any condensation in the instrument. In addition, the line may be cooled to further dry the gas before it enters the gas analyzers. The two gas analyzers are interfaced with two solenoid-type valves, one permitting the injection of pure oxygen into the system and the other one to route the process gas stream through the $CO_2$ removal reactor 9, whenever a critical $CO_2$ concentration in the gas system has been reached. Alternatively, the system may be operated by continually passing off-gases through the $CO_2$ removal reactor, hence specifying a lower equilibrium carbon dioxide partial pressure in the recirculated gas stream. Any non-biodegradable volatile organics can be removed by routing a $CO_2$-lean gas bleed stream through an activated carbon adsorption column (not shown), if this becomes necessary.

A centrifugal displacement type vacuum pump which can handle a mixture of air and water is used to recirculate the gas stream. Since the cooling water within the casing of this compressor will be contaminated by the volatile organics in the process gases, it may be kept in a closed loop and cooled by a seal water air cooler (not shown). From time to time a small bleed stream is removed from the loop and sent to wastewater treatment. Makeup water is added to the cooling loop to balance any system blowdowns.

The approach discussed in connection with the Figure involves the addition of a large population of hydrocarbon degrading bacteria (in the form of activated sludges from petrochemical treatment bioprocesses) to the hazardous waste material, forming a slurry of waste and microorganisms which can be reacted in stirred tanks to effect either an aerobic or anaerobic degradation at temperatures optimal for microbial growth and substrate utilization. This assures that a sufficient inventory of acclimated microorganisms is present to achieve the full potential of the bioremediation process. An aerobic or oxidative microbial pathway is deemed optimum for the degradation of organics typical of most hazardous wastes (i.e., volatile, semi-volatile, and some halogenated organics). These particulars coupled with the understanding that the efficiency of aerobic biodegradation of organics is also a function of mixing for optimum substrate-microorganism contact, oxygenation to assure that aerobic degradation is the dominant mechanism for removal, and adequate nutrients (i.e., carbon, nitrogen, and phosphorus) for the synthesis of cell material. Total degradation of an organic compound occurs through a series of metabolic reactions among different microorganisms.

The hypothesized mechanism for oxidative biodegradation of hazardous wastes is an initial dissolution and/or dispersal of the waste and waste constituents into the aqueous-phase, followed by actual degradation of the waste constituents through normal aerobic metabolisms. The apparent dissolution and/or dispersal of waste constituents results from the formation of microbial solvents and surfactants that act as emulsifiers dispersing the more oleophilic constituents into the aqueous phase. The compounds which partition strongly with the oil phase (e.g., polynuclear aromatics, polychlorinated biphenyls) are slowest to disperse within the bioreactor and are, consequently, the slowest to degrade. Compounds with high vapor pressures (especially those with a low water solubility) will be rapidly dispersed within the bioreactor and are more likely to be stripped from solution during the early stages of the oxidations unless off-gas recirculation is used to increase the residence time of the volatiles in the bioreactor. Therefore, the dissolution and conversion of the most slowly metabolizable substances determines the total reaction period for slurry biodegradation of hazardous waste constituents.

In accordance with the invention, the maintenance of a continuous or semicontinuous feed to a series of stirred tank reactors (thus approaching a plug flow condition) provides a high substrate to microorganism ratio initially while tapering this ratio through the reactor system, thereby providing optimal biodegradation kinetics for constituent removal. The use of bioslurry recirculation to control the substrate to microorganism ratio of the process during continuous treatment and provide a renewable process much in the same manner as activated sludge treatment. The maintenance of a high oxygen transfer efficiency during aeration in a low hydraulic shear environment to promote the development of a large population of microorganisms that will form flocculent suspensions (necessary to attain a microorganism separation after treatment), but still maintain sufficient mixing to keep a dense slurry (e.g., 40% solids) in suspension. The airlift loop reactor provides this environment when the downcomer is at least a thousand times the cross-sectional area of the riser, and a gas stream is diffused into the downcomer in a manner that achieves fine bubble aeration for gentle mixing and waste dissolution, and that this mixing is promoted by the use of low-speed axial flow turbines located in the downcomer.

Pursuant to a further important aspect of the present invention, off-gas recirculation is used to collect and return volatile hydrocarbons to the reactor system for treatment. Most aromatic hydrocarbons can be biodegraded in a continuous throughput system provided that the residence time in contact with the microbes is greater than the minimum allowable kinetic rate of decomposition (i.e., usually 0.2 to 0.5 hr$^{-1}$ for aromatic hydrocarbons). Specifically, it is seen that the process off-gas at 17 after passing through a vacuum vent regulator 8 and $CO_2$ removal reactor 9, is returned as $CO_2$ lean recycle gas (also oxygen-lean) via line 25 and line 27 to the several reactors. Additional oxygen may be fed in via line 26 provided by an oxygen plant 12, if required. Use Of off-gas recirculation to collect and return the more volatile toxic constituents, typically benzene, toluene, xylenes, and naphthalene to the reactor system, enables a more complete microbial degradation. Additionally, this provides both volatile organic compound emission control and a mechanism for enhancement of microbial degradation of the more persistent organic compounds, for example, higher molecular weight PAHs such as benzo(a)anthracene, benzo(b)fluoranthene. Thus, the off-gas recirculation system removes carbon dioxide from the gas stream and provides for oxygen addition as required to meet the metabolic needs of the process microbes.

It is a further aspect of the invention that the process can also be operated under anaerobic conditions by not providing oxygen to the recirculated off-gas when returned to the reactors. Here the principal modes of energy-yielding metabolism may be either fermentation or anaerobic respiration. In fermentation, organic compounds serve both as electron donors and as electron acceptors. Usually two different metabolites derived from a fermentable substrate give rise to a mixture of end-products, some of which are more oxidized than the substrate and others more reduced. In anaerobic respiration, organic compounds serve as electron donors and an oxidized inorganic compound other than oxygen serves as ultimate electron acceptor. The compounds that can so act are sulfates, nitrates, and carbonates.

Portions of the process are operated under anaerobic conditions to achieve generation of microbial solvents for effective waste dissolution and/or to effect a degree of reductive dehalogenation of certain purgeable halocarbons and polychlorinated biphenyls to enhance the aerobic biodegradations that occur in later stages of the treatment train.

A closed loop off-gas recirculation system also permits the addition of selected volatile aromatic hydrocarbons to the process gas stream 29. These are added primarily as cosubstrates to stimulate the growth of the principal genera of bacteria used in the process, Pseudomonas and Acinetobacter. The volatile aromatic hydrocarbon cosubstrates of choice are toluene and paraxylene because they act as both growth substrates and cometabolites for enhanced polynuclear aromatic hydrocarbon biodegradation. The preferred method of addition is as liquid reagent metered to the second stage bioreactor. Because of their volatility, both toluene and p-xylene will quickly enter the gaseous phase and uniformly distribute throughout the off-gas recirculation system.

Cosubstrates may also be added directly to the slurry phase of the process, depicted in the Figure as growth nutrient additives 30. These are compounds that the microbes can use as a nutrient or an energy source. The compounds of choice include phenolics such as simple phenol and para-cresol; phenyldecane; hexadecane; paranaphthalic acid; biphenyl; benzoate; camphor; pyrene; and butanone. Generally, growth nutrient addition occurs beyond the second stage bioreactor.

All of these compounds act as growth substrates in addition to cometabolizing the biodegradation of normally persistent hazardous waste constituents (e.g., benzo(a)pyrene, benzo(b)fluoranthene). It is an important aspect of the invention that growth substrates are provided to the microorganisms to enhance the biodegradation of persistent hydrocarbons through a rapid rise in the rate of biodegradation that results from the presence of growth stimulating nutrient additives. It is generally understood that a cometabolizing microbe does not derive useful energy from the oxidation of cosubstrates alone. Thus, bacteria numbers of a cometabolizing population may not rise rapidly with time or achieve a high rate of biodegradation without the presence of the aforementioned growth nutrient additives.

The microorganisms that form the flocculent suspensions particularly in the second and subsequent stages are primarily responsible for waste dissolution and are facultative anaerobes, i.e. they perform aerobic respiratory metabolism in an aerobic environment but will also grow under anaerobic conditions, using as a source of energy either fermentation or anaerobic respiration. It is believed that in the waste dissolution reactor the primary mode of energy yielding metabolism is fermentation in that the average oxidation level of the end product is identical with that of the untreated waste.

The use of a closed loop design as in the present system allows operation of the bioreactors under anaerobic conditions with the same ease as under aerobic conditions. Oxygen may only be omitted from the closed loop which rapidly results in an anoxic environment in the bioreactors. It is a further aspect of the invention that individual bioreactors may be segregated from the main process off-gas recirculation loop and placed under anaerobic conditions to achieve specific process performance objectives (e.g., reductive dehalogenation, biosolvent production). This is accomplished by installing an additional centrifugal displacement type vacuum pump and off-gas management system which is dedicated to the anaerobic reactor(s). One aspect of the present process can involve the use of alternating anoxic and aerobic stirred tank reactors to effect a combination reductive and oxidative dehalogenation of chlorinated hydrocarbons in a hazardous waste and/or soil. In practice it is found that when utilizing such an approach primarily the lower chlorinated isomers are degraded by the principal genera of bacteria used in the process under combined anoxic and aerobic conditions (e.g., chlorinated isomers of PCB with molecular weight less than pentachlorobiphenyl). Nonetheless, anaerobic treatment or more accurately fermentation does occur in the anoxic reactors which results in enhanced treatment of the constituents in the tarry oily waste as well as the tars and oils in the subsequent aerobic stages of the process.

The system permits operation under strict anaerobiosis to effect a condition of reductive dehalogenation of PCB congeners with molecular weights greater than pentachlorobiphenyl. This is a non-methanogenic condition since methane production would not likely occur. The anaerobic stage is followed by a series of aerobic stages, as discussed above.

EXAMPLE 1

A system as depicted in the Figure operating in accordance with the foregoing principles was utilized in the treatment of a waste material from petroleum and petrochemical processing. The waste was a combination of tarry-oily sludge and oil contaminated soil. The tarry-oily sludge was 47 percent solids and 25 percent petroleum hydrocarbon by weight. The hydrocarbon contamination in the sludge was composed of 25 percent saturates, 40 percent aromatics, and 35 percent resins. The toxic organic pollutants identified in both the tarry-oily sludge and oil contaminated soil were petroleum aromatics, polynuclear aromatic hydrocarbons, purgeable halocarbons, and phthalates.

This waste combination was treated by the invention at ambient temperatures (i.e., 23°-25° C.) using an overall system hydraulic residence time of 30 days. The process utilized a first-stage waste dissolution reactor and three aerobic bioreactors operated in series. The process was acclimated with hydrocarbon-utilizing bacteria of the genera Pseudomonas and Acinetobacter. The system maintained off-gas recirculation and aerobic conditions in the second-, third-, and fourth-stages of the process throughout the test period. The waste dissolution reactor was operated under anaerobic conditions throughout the test period. Nitrogen and phosphorus levels were adjusted within the system to optimize biosolvent and biosurfactant production in accordance with the invention.

Mixing in the waste dissolution reactor was accomplished using a low-speed radial-flow turbine, while the second-, third-, and fourth-stage bioreactors were mixed using a combination airlift and axial-flow turbine. The speeds of the axial-flow turbines decreased with increasing reactor stage number.

The slurry concentration in the waste dissolution reactor was maintained at 40 percent solids. Slurry levels in the second-, third-, and fourth-stage bioreactors equalled 37, 29, and 16 percent solids, respectively. Equilibrium slurry-phase chemical oxygen demand levels in the second-, third-, and fourth-stage bioreactors were 250,000, 198,000, and 110,000 mg/L, respectively. Slurry-phase hydrocarbon oil concentrations varied from a high of 12 percent in the waste dissolution reactor to a low of 1.9 percent in the fourth-stage bioreactor. Overall system chemical oxygen demand and hydrocarbon oil removals were 84 and 56 percent, respectively.

The process was operated for 90 days under a semi-continuous waste load condition (i.e., six equal feed cycles were provided each day). Effluent quality was sampled on days 60 and 90 for toxic organic constituents. The results of these analyses are presented in Tables III and IV, for volatile and semi-volatile hydrocarbons, respectively. These data indicate that most of the petroleum aromatics, purgeable halocarbons, polynuclear aromatic hydrocarbons, and phthalates in the combination waste were reduced to low levels in the effluent from the process. Low levels of aromatic hydrocarbons and purgeable halocarbons also were found in the vapor phase of the off-gas recirculation loop.

TABLE III

Process Performance for Volatile Hydrocarbon Treatment

| Compound | Tarry-Oily Sludge Average | Tarry-Oily Sludge Range | Contaminated Soil[a] | Combined Waste[a,b] | Biologically Treated Residue[a] Average | Biologically Treated Residue[a] Range | Vapor Phase Off-Gas Recirculation Loop[c] Average | Vapor Phase Off-Gas Recirculation Loop[c] Range |
|---|---|---|---|---|---|---|---|---|
| Acetone | 21.8 | ND–41.5 | ND | 17.4 | ND | — | NA | — |
| Benzene | 59.1 | 9.0–177.7 | 118.5 | 71.0 | 0.09 | ND–0.12 | 0.011 | 0.003–0.018 |
| Chlorobenzene | 3.3 | ND–6.2 | ND | 2.6 | ND | — | ND | — |
| 1,1-Dichloroethane | 0.7 | ND–1.2 | ND | 0.6 | ND | — | ND | — |
| 1,2-Dichloroethane | ND | ND–1.0 | ND | ND | ND | — | ND | ND–0.001 |
| Trans-1,2-Dichloroethene | ND | ND–1.5 | ND | ND | ND | — | ND | — |
| Ethylbenzene | 245.3 | 40.9–648.9 | 164.6 | 229.2 | 0.09 | 0.05–0.13 | ND | ND–0.001 |
| 1,2-Dichloropropane | ND | ND–0.6 | ND | ND | ND | — | ND | — |
| 2-Hexanone | 8.0 | ND–20.3 | ND | 6.4 | ND | — | NA | — |
| Methyl ethyl ketone | 87.1 | ND–223.4 | ND | 69.7 | ND | ND–0.42 | NA | — |
| 4-Methyl-2-pentanone | 73.3 | ND–185.1 | 13.7 | 61.4 | ND | — | NA | — |
| Methylene Chloride | ND | ND–1.3 | ND | ND | 1.18 | ND–2.13 | 0.032 | 0.025–0.039 |
| Styrene | 178.3 | 8.6–606.4 | 51.5 | 152.9 | ND | ND–0.07 | ND | — |
| Tetrachloroethene | 1.1 | ND–1.4 | 23.8 | 5.6 | 0.59 | 0.32–0.88 | ND | ND–0.002 |
| Toluene | 309.6 | 136.3–659.6 | 144.6 | 276.6 | 0.13 | 0.08–0.16 | 0.013 | 0.007–0.019 |
| Trichloroethene | 1.8 | ND–2.4 | 5.9 | 2.6 | ND | ND–0.09 | ND | ND–0.002 |
| Xylenes | 566.8 | 41.8–1883.0 | 553.8 | 564.2 | 0.23 | 0.11–0.36 | ND | ND–0.004 |

[a]Units: mg contaminant/kg waste, reported on a dry weight basis.
[b]Combined waste is a mixture of 28% soil and 72% tarry-oily sludge (by weight).
[c]Units: ppmv
ND means not detected.
NA means not analyzed.

TABLE IV

Process Performance for Semi-Volatile Hydrocarbon Treatment

| Compound | Tarry-Oily Sludge[a] Average | Tarry-Oily Sludge[a] Range | Contaminated Soil[a] | Combined Waste[a,b] | Biologically Treated Residue[a] |
|---|---|---|---|---|---|
| Acenaphthene | ND | — | 19.7 | 3.9 | ND |
| Acenaphthylene | ND | ND–7.0 | 4.3 | 0.9 | ND |
| Anthracene | 34.4 | 51–76.6 | 6.2 | 28.8 | ND |
| Benzo(a)anthracene | ND | — | 12.5 | 2.5 | ND |
| Butylbenzylphthalate | 34.0 | 11.5–66.0 | 14.0 | 30.0 | ND |
| Chrysene | 36.9 | ND–61.7 | 13.1 | 32.1 | ND |
| Di-n-octylphthalate | ND | ND–61.7 | 12.7 | 2.5 | ND |
| Dibenzofuran | ND | — | 5.8 | 1.2 | ND |
| Dibutylphthalate | ND | ND–42.6 | 28.6 | 5.7 | ND |
| 1,4-Dichlorobenzene | ND | — | 29.2 | 5.8 | ND |
| 2,4-Dimethylphenol | 188.3 | 36.3–489.4 | 29.2 | 156.5 | ND |
| 2,4-Dinitrotoluene | ND | — | 20.0 | 4.0 | ND |
| Diphenylamine | ND | — | 132.3 | 26.5 | ND |

TABLE IV-continued

| | Process Performance for Semi-Volatile Hydrocarbon Treatment | | | | |
|---|---|---|---|---|---|
| | Tarry-Oily Sludge[a] | | Contaminated | | Biologically |
| Compound | Average | Range | Soil[a] | Combined Waste[a,b] | Treated Residue[a] |
| bis(2-ethyl hexyl)phthalate | 409.7 | 62.7-1085.1 | 79.2 | 343.6 | ND |
| Fluoranthene | 49.8 | 3.9-113.8 | 20.8 | 44.0 | ND |
| Fluorene | ND | ND-115.3 | ND | ND | ND |
| 2-methylnaphthalene | 176.5 | 40.0-383.0 | 51.5 | 151.5 | ND |
| 2-methylphenol | ND | ND-191.5 | 17.7 | 3.5 | ND |
| 4-methylphenol | ND | ND-542.6 | 63.8 | 12.8 | ND |
| N-Nitrosodiphenylamine | ND | ND-287.2 | 132.3 | 26.5 | ND |
| Naphthalene | 172.6 | 18.4-446.8 | 49.2 | 147.9 | ND |
| Phenanthrene | 95.4 | 6.8-244.7 | 44.6 | 85.2 | ND |
| Phenol | ND | ND-3723.4 | 492.3 | 98.5 | ND |
| Pyrene | 31.0 | 5.0-68.1 | 24.0 | 29.6 | ND |
| 1,2,4-Trichlorobenzene | ND | — | 27.7 | 5.5 | ND |

[a]Units: mg contaminant/kg waste, reported on a dry weight basis.
[b]Combined waste is a mixture of 28% soil and 72% tarry-oily sludge (by weight).
ND means not detected.

EXAMPLE 2

The invention, as described in the foregoing example, was modified to incorporate an intermediate anoxic reactor as the third-stage bioreactor. This was accomplished by installing a separate anoxic off-gas recirculation loop around the third-stage bioreactor, thus permitting reactor dissolved oxygen levels to fall below 0.5 mg/L in the slurry mixture. This reactor was maintained under essentially anaerobic conditions throughout the test period.

The combination waste described in the previous example was fed to this system for 60 days, after which vapor phase sample analysis was conducted on both the aerobic and anaerobic off-gas recirculation loops. The results are as follows:

| Compounds | Aerobic System Loop (ppbv) | Anaerobic System Loop (ppbv) |
|---|---|---|
| Halogens | | |
| carbon tetrachloride | 0.1 | ND |
| chloroform | 2.4 | 1.1 |
| chloromethane | 0.3 | ND |
| 1,1-dichloroethane | 0.1 | 0.1 |
| 1,2-dichloroethane | 0.9 | 0.1 |
| 1,1-dichloroethylene | 0.2 | 0.3 |
| T-1,2-dichloroethylene | 0.3 | 0.1 |
| 1,2-dichloropropane | ND | 0.2 |
| methylene chloride | 24.8 | 15.4 |
| tetrachloroethylene | 2.3 | 24.3 |
| 1,1,1-trichloroethane | 5.6 | 5.8 |
| trichloroethylene | 2.4 | 4.1 |
| trichlorofluoromethane | 0.6 | 0.2 |
| vinyl chloride | 0.5 | 0.8 |
| Freons | | |
| dichlorodifluoromethane | 0.8 | ND |
| Hydrocarbons | | |
| benzene | 3.4 | 10.0 |
| toluene | 6.8 | 42.7 |
| ethylbenzene | 0.9 | 6.9 |
| p-xylene + m-xylene | 2.6 | 14.9 |
| styrene | ND | 8.5 |
| o-xylene | 1.8 | 4.6 |

These data are representative of the volatile organic compound (VOC) levels in the off-gas recirculation loops after approximately 60 days of semicontinuous feeding under quasi-steady-state conditions. They show that the aerobic system loop has lower concentrations of VOCs than the anaerobic system loop. However, a greater number of halogenated hydrocarbons were identified in the off-gas from the aerobic system loop at slightly higher concentrations than those found in the anaerobic system loop. These data suggest that dehalogenation of some purgeable halocarbons are occurring in the system when an intermediate anoxic bioreactor is incorporated in the waste treatment train.

To assess whether VOCs were lost from the treatment system by way of sorption in the $CO_2$ scrubber solution, samples of the scrubber solution were collected for VOC analysis. The results of this analysis are as follows:

| | Concentration[a] ($\mu$g/L) | Solubility in Water at 25° C.[b] ($\mu$g/L) |
|---|---|---|
| benzene | 1.5 | 1,800,000 |
| toluene | 2.8 | 535,000 |
| ethylbenzene | ND | 152,000 |
| xylenes | ND | NA |
| styrene | ND | 300,000 |
| methyl ethyl ketone | 10.3 | NA |
| 4-methyl-2-pentanone (MIBK) | 21.5 | NA |
| methylene chloride | 21.0 | 16,700,000 |
| tetrachloroethene | 3.6 | 200,000 |
| 1,1,1-trichloroethane | 3.8 | 4,400,000 |
| trichloroethene | 1.4 | 1,100,000 |

[a]Data are an average of two samples
[b]EPA Treatability Data, EPA-600/2-82-001a
NA means not available.
ND means not detected.

These data indicate that relatively low concentrations of volatile compounds are present in the $CO_2$ scrubber solution, thus confirming the effectiveness of the microbial treatment process.

EXAMPLE 3

A system as depicted in the Figure operating in accordance with the invention was utilized in the treatment of a tarry-oily sludge from a hazardous waste site. The waste consists of tars from ethylbenzene-styrene production mixed with polychlorinated biphenyl laden transformer fluids. The waste contained 30% hydrocarbon oils by weight and a number of volatile aromatics typical of petroleum hydrocarbons. The toxic organics of concern were the Aroclors PCB 1016 and PCB 1254, benzene, toluene, ethylbenzene, styrene, and the xylenes.

The tarry-oily sludge was treated by the invention at ambient temperatures (i.e., 23°-25° C.) using an overall system hydraulic residence time of 65 days. The process utilized a first-stage waste dissolution reactor and two aerobic bioreactors operated in series. The process was acclimated with hydrocarbon-utilizing bacteria of the genera Pseudomonas and Acinetobacter. The system maintained off-gas recirculation and aerobic conditions in the second- and third-stages of the process throughout the test period. The waste dissolution reactor was operated under anaerobic conditions throughout the test period. Nitrogen and phosphorus levels were adjusted within the system to optimize biosolvent and biosurfactant production in accordance with the invention.

Mixing in the waste dissolution reactor was accomplished using a low-speed radial-flow turbine, while the second- and third-stage bioreactors were mixed using a combination airlift and axial-flow turbine. The speeds of the axial-flow turbines were decreased with increasing reactor stage number.

The slurry concentration in the waste dissolution reactor was maintained at 35% solids. Slurry levels in the second- and third-stage bioreactors equalled 27 and 21% solids, respectively. Slurry-phase hydrocarbon oil concentrations varied from a high of 30% in the waste dissolution reactor to a low of 3.2% in the third-stage bioreactor after 130 days of semicontinuous feeding (i.e., six equal feed cycles were provided each day).

The petroleum aromatic hydrocarbons were found to be at negligible levels in the second- and third-stage bioreactors after 130 days of system operation (i.e., two system residence times). The polychlorinated biphenyls in the tarry-oily waste were reduced as follows:

| Parameter[a] | Waste Dissolution Reactor (µg/kg) | Biologically Treated Residue (µg/kg) |
|---|---|---|
| Congeners | | |
| Monochlorobiphenyls | 132 | ND |
| Dichlorobiphenyls | 521 | 168 |
| Trichlorobiphenyls | 9,412 | 4,053 |
| Tetrachlorobiphenyls | 17,059 | 11,579 |
| Pentachlorobiphenyls | 6,765 | 4,316 |
| Hexachlorobiphenyls | 2,147 | 2,079 |
| Heptachlorobiphenyls | 500 | 468 |
| Octachlorobiphenyls | ND | ND |
| Nonachlorobiphenyls | ND | ND |
| Total Congeners | 36,536 | 22,663 |
| Aroclors | | |
| PCB 1016 | 29,412 | ND |
| PCB 1254 | 30,000 | 28,421 |
| Total Aroclors | 59,412 | 28,421 |

[a]All data are presented on a dry weight basis and are determined from the average of sample and sample duplicate analyses.

The polychlorinated biphenyl removal data indicate that the microbial degradations occurred primarily with the lower chlorinated isomers of PCB as is evident from an examination of the congener data. These data suggest that the mono- through pentachlorobiphenyls were partially biodegraded in the process. This is verified by an examination of the Aroclor data. Here it is apparent that the low molecular weight Aroclor (PCB 1016) was removed from the waste, or at least, transformed to some nondetectable form; and the higher molecular weight Aroclor (PCB 1254) may not have been degraded to any significant degree under aerobic conditions.

EXAMPLE 4

The same tarry-oily sludge presented in the previous example was treated under anoxic conditions by the invention at ambient temperatures (i.e., 23°–25° C.) using an overall system hydraulic residence time of 65 days. The process utilized three anoxic bioreactors operated in-series with the first-stage reactor used primarily for waste dissolution. The process was acclimated with hydrocarbon-utilizing bacteria of the genera Pseudomonas and Acinetobacter. The system maintained off-gas recirculation and anaerobic conditions in each reactor stage throughout the test period. Nitrogen and phosphorus concentrations were amended to levels which optimize biosolvent production in accordance with the invention.

Mixing in the first-stage reactor was accomplished using a low-speed radial-flow turbine, while the second- and third-stage bioreactors were mixed using a combination airlift and axial-flow turbine.

Slurry concentrations varied from a high of 35% solids in the first-stage to a low of 25% solids in the last reactor stage. Slurry-phase hydrocarbon oil concentrations varied from a high of 30% in the first-stage reactor to a low of 15.2% in the third-stage anoxic bioreactor after 130 days of semicontinuous feeding (i.e., six equal feed cycles were provided each day).

After 130 days of system operation (i.e., two system residence times), the petroleum aromatic hydrocarbons were found to be at negligible levels in the second- and third-stage anoxic bioreactors. The polychlorinated biphenyls in the tarry-oily waste were reduced as follows:

| Parameter[a] | First-Stage Bioreactor (µg/kg) | Second-Stage Bioreactor (µg/kg) | Third-Stage Bioreactor (µg/kg) |
|---|---|---|---|
| Congeners | | | |
| Monochlorobiphenyls | 1,923 | 410 | ND |
| Dichlorobiphenyls | 10,385 | 5,385 | 4,839 |
| Trichlorobiphenyls | 13,615 | 6,539 | 6,613 |
| Tetrachlorobiphenyls | 14,692 | 8,333 | 7,419 |
| Pentachlorobiphenyls | 4,923 | 2,436 | 1,129 |
| Hexachlorobiphenyls | 1,569 | ND | ND |
| Heptachlorobiphenyls | 585 | ND | ND |
| Octachlorobiphenyls | 127 | ND | ND |
| Nonachlorobiphenyls | ND | ND | ND |
| Total Congeners | 47,819 | 23,103 | 20,000 |
| Aroclors | | | |
| PCB 1016 | 82,000 | 71,795 | 18,226 |
| PCB 1254 | 68,000 | 23,205 | 4,516 |
| Total Aroclors | 150,000 | 95,000 | 22,742 |

[a]All data are presented on a dry weight basis and are determined from the average of sample and sample duplicate analyses.

The congener data suggest that under anoxic conditions, the higher chlorinated isomers of PCB will be reduced by the process and that some low molecular weight isomers are also removed, albeit at a slower rate. The effect is more apparent with the Aroclors where the high molecular weight Aroclor (PCB 1254) was reduced to lower concentrations than the lower molecular weight Aroclor (PCB 1016).

These data suggest that PCB biodegradation may be improved by cycling within the process a single microbial consortium of facultative anaerobes with specialized metabolic characteristics through different reaction environments (i.e., anoxic, aerobic, anoxic, aerobic, etc.). This may be accomplished primarily through the mechanism of reactor off-gas recirculation as described herein.

While the present invention has been particularly set forth in terms of specific embodiments thereof, it will be understood in view of the instant disclosure, that numerous variations upon the invention are now enabled to those skilled in the art, which variations yet reside within the scope of the present teaching. Accordingly, the invention is to be broadly construed, and limited only by the scope and spirit of the claims now appended hereto.

What is claimed is:

1. A method for improved slurry-phase bioremediation treatment of organic sludge and mixtures of organic sludge and organic-contaminated soils by dissolving the contaminants into an aqueous phase and microbially degrading same; comprising the steps of:
   (a) forming a high solids slurry of said sludge and soils with water and an active bioslurry consisting of large populations of acclimated hydrocarbon-utilizing bacteria and small amounts of biodegradation residue; said bacteria being selected from the genera Pseudomonas and Acinetobacter, and being capable of producing extracellular long-chain hydrocarbon-emulsifying and -solubilizing agents for decreasing aqueous surface tension and lowering interfacial tension between oil and water;
   (b) passing said high solids slurry through a plurality of in-series bioreactors in each of which a low hydraulic shear is maintained to promote the development of a large population of microorganisms that will form flocculent suspensions; the first stage bioreactor in said series being a waste dissolution reactor operated under anoxic conditions to form a stable emulsion through the presence of said hydrocarbon-emulsifying and hydrocarbon-solubilizing agents produced by said bacteria;
   (c) continuously or semicontinuously flowing the output from said series of bioreactors to a liquid-solids separator to partition the mixed liquor bioslurry from the biodegraded waste residue;
   (d) returning said mixed liquor bioslurry containing small amounts of biodegradation residue to the slurry of step (a) for recycling; and
   (e) recirculating off-gas components from said system including one or more members of the group consisting of benzene, toluene, xylenes, and naphthalene back to one or more of said bioreactors, to return high volatility toxic constituents for increased microbial degradation and control of volatile toxic constituents emissions from the process.

2. A method in accordance with claim 1, wherein the total solids in said slurry is between 25 and 45% by weight of the slurry, of which 70 to 80% is tarry-oily sludge and/or soil, and 20 to 30% is active bioslurry, on a dry weight basis.

3. A method in accordance with claim 1, wherein in step (b) the aeration and mixing intensity in each bioreactor is controlled to effect consecutively lower hydraulic shear levels among said series of bioreactors, to thereby enhance separation of treated waste residue from the mixed liquor bioslurry at the separation step (c).

4. A method in accordance with claim 1, wherein hydrocarbon-emulsifying and -solubilizing agents are produced under conditions of either anoxic or aerobic unbalanced growth of facultative anaerobic bacteria.

5. A method in accordance with claim 1, wherein in step (e) the process in the bioreactors following said first stage bioreactor is operated under either aerobic or anaerobic conditions by either providing or not providing oxygen to the recirculated off-gas when returned to the reactors.

6. A method in accordance with claim 5, wherein portions of the process are operated under anaerobic conditions to achieve generation of microbial solvents for waste dissolution and/or to effect a degree of reductive dehalogenation of selected purgeable halocarbons and polychlorinated biphenyls.

7. A method in accordance with claim 1, wherein in step (d) bioslurry is recirculated to control the substrate to microorganism ratio of the process during continuous or semicontinuous treatments, to thereby provide a renewable process.

8. A method in accordance with claim 1, wherein mixing in the first-stage waste dissolution reactor is accomplished using low-speed radial-flow turbines; and wherein subsequent bioreactor stages are mixed using combinations of airlifts and axial-flow turbines operated at speeds which diminish with increasing reactor stage number.

9. A method in accordance with claim 1, wherein one or more growth stimulating nutrient additives are added to said high solids slurry, thereby effecting enhanced biodegradation of persistent compounds through a rapid rise in the rate of biodegradation.

10. A method in accordance with claim 9, wherein said growth stimulating nutrient additives are selected from one or more members of the group consisting of the compounds toluene; para-xylene; phenol; para-cresol; phenyldecane; hexadecane; para-naphthalic acid; biphenyl; benzoate; camphor; pyrene; and butanone; said additives providing the microorganisms with energy and acting as cosubstrates.

11. A method in accordance with claim 10, wherein said nutrient additive comprises toluene.

12. A method in accordance with claim 10, wherein said nutrient additive comprises para-xylene.

13. A system for improved slurry-phase bioremediation treatment of organic sludge and mixtures of organic sludge and organics-contaminated soils by dissolving the contaminants into an aqueous phase and microbially degrading same; comprising:
   (a) a plurality of in-series bioreactors in each of which a low hydraulic shear is maintained;
   (b) means for forming a high solids slurry of said sludge and soils with water and an active bioslurry consisting of large populations of acclimated hydrocarbon-utilizing bacteria and passing said high solids slurry through said plurality of in-series reactors to promote the development of a large population of microorganisms that will form flocculent suspensions;
   (c) a liquid-solids separator for partitioning the mixed liquor bioslurry from the biodegraded waste residue;
   (d) means for continuously or semicontinuously flowing the output from said series of bioreactors to said liquid-solids separator;
   (e) means for returning said mixed liquor bioslurry containing small amounts of biodegradation residue to the means of step (a) for recycling;
   (f) means for recirculating off-gas components from said system back to one or more of said bioreactors, to return high volatility toxic constituents for increased microbial degradation and control of volatile toxic constituent emissions from said system; and (g) means for adding directly to the high solids slurry one or more growth stimulating nutrient additives, thereby effecting enhanced biodegradation of persistent compounds through a rapid rise in the rate of biodegradation.

14. A system in accordance with claim 13, wherein said bioreactors are stirred tank reactors.

15. A system in accordance with claim 13, wherein the aeration and mixing intensity of each bioreactor is controlled to effect consecutively lower hydraulic shear levels among said series of bioreactors, to thereby enhance separation of treated waste residue from the mixed liquor bioslurry at said separator.

16. A system in accordance with claim 13, further including means for establishing alternating anoxic and aerobic conditions among successive of at least some of said series of bioreactors.

17. A system in accordance with claim 13, wherein at least some of said bioreactors are airlift reactors.

* * * * *

UNITED STATES PATENT AND TRADEMARK OFFICE
CERTIFICATE OF CORRECTION

PATENT NO. : 5,232,596
DATED : August 3, 1993
INVENTOR(S) : Frank J. Castaldi

It is certified that error appears in the above-indentified patent and that said Letters Patent is hereby corrected as shown below:

The title page, should be deleted to appear as per attached title page.

The sheet of drawing should be deleted to appear as per attached sheet.

In the Abstract, line 16, after the word "residue" insert --.--.

Signed and Sealed this

Twenty-sixth Day of April, 1994

Attest:

BRUCE LEHMAN

Attesting Officer          Commissioner of Patents and Trademarks

United States Patent [19]

Castaldi

[11] Patent Number: 5,232,596
[45] Date of Patent: Aug. 3, 1993

[54] BIO-SLURRY REACTION SYSTEM AND PROCESS FOR HAZARDOUS WASTE TREATMENT

[75] Inventor: Frank J. Castaldi, Austin, Tex.
[73] Assignee: Radian Corporation, Austin, Tex.
[21] Appl. No.: 773,344
[22] Filed: Oct. 7, 1991
[51] Int. Cl.$^5$ ............................................... C02F 3/34
[52] U.S. Cl. .................................... 210/603; 210/805
[58] Field of Search ............... 423/DIG. 17; 210/602, 210/805, 603, 617, 742, 621, 760, 611

[56] References Cited

U.S. PATENT DOCUMENTS

| | | | |
|---|---|---|---|
| 4,649,117 | 3/1987 | Familletti | 435/313 |
| 4,728,082 | 3/1988 | Emmett et al. | 266/168 |
| 4,729,788 | 3/1988 | Hutchins et al. | 75/118 R |
| 4,732,608 | 3/1988 | Emmett et al. | 75/101 R |
| 5,057,284 | 10/1991 | Emmett, Jr. et al. | 423/DIG. 17 X |

FOREIGN PATENT DOCUMENTS

| | | |
|---|---|---|
| 0197299 | 10/1986 | European Pat. Off. |
| 0379121 | 7/1990 | European Pat. Off. |
| 4013552 | 10/1991 | Fed. Rep. of Germany |
| 8704694 | 8/1987 | PCT Int'l Appl. |
| 8906992 | 8/1989 | PCT Int'l Appl. |

Primary Examiner—Frank Spear
Assistant Examiner—Frank Spear
Attorney, Agent, or Firm—Klauber & Jackson

[57] ABSTRACT

A method for improved slurry-phase bioremediation treatment of organic sludge and mixtures of organic sludge and organics-contaminated soils by dissolving the contaminants into an aqueous phase and microbially degrading same. A high solids slurry of the sludge and soils is formed with water and an active bioslurry consisting of large populations of acclimated hydrocarbon-utilizing bacteria and small amounts of biodegradation residue. The slurry is passed through a plurality of in-series bioreactors in each of which a low hydraulic shear is maintained to promote the development of a large population of microorganisms that will form flocculent suspensions. The output from the series of bioreactors is flowed continuously or semicontinuously to a liquid-solids separator to partition the mixed liquor bioslurry from the biodegraded waste residue. The mixed liquor bioslurry containing small amounts of biodegradation residue is returned to the slurry being processed for recycling. Off-gas components from the system are recirculated back to one or more of the bioreactors, to return high volatility toxic constituents for increased microbial degradation and control of volatile toxic constituent emissions from the process. The related system is also disclosed and claimed.

17 Claims, 1 Drawing Sheet

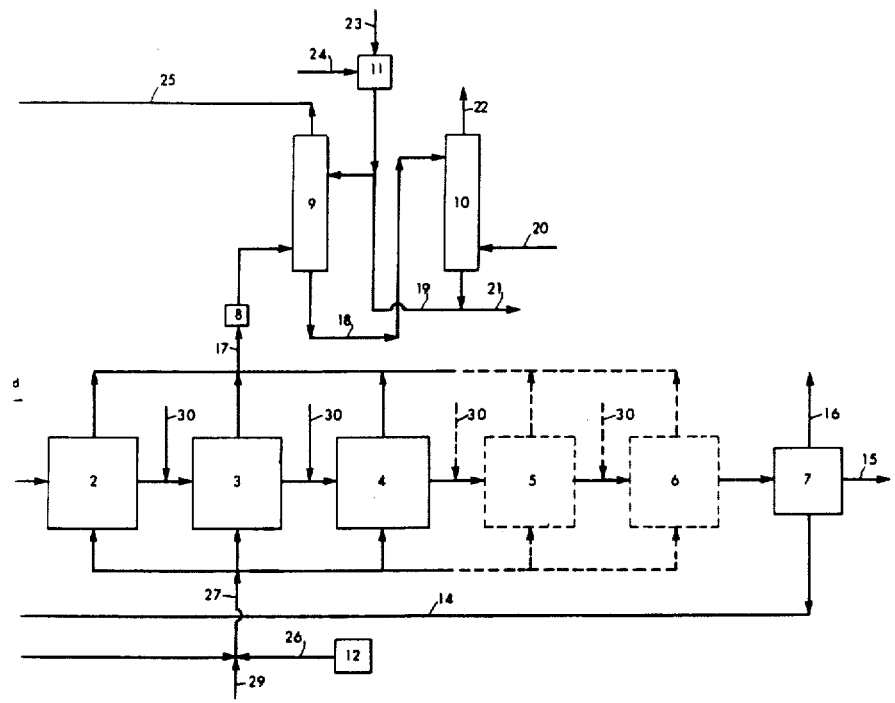

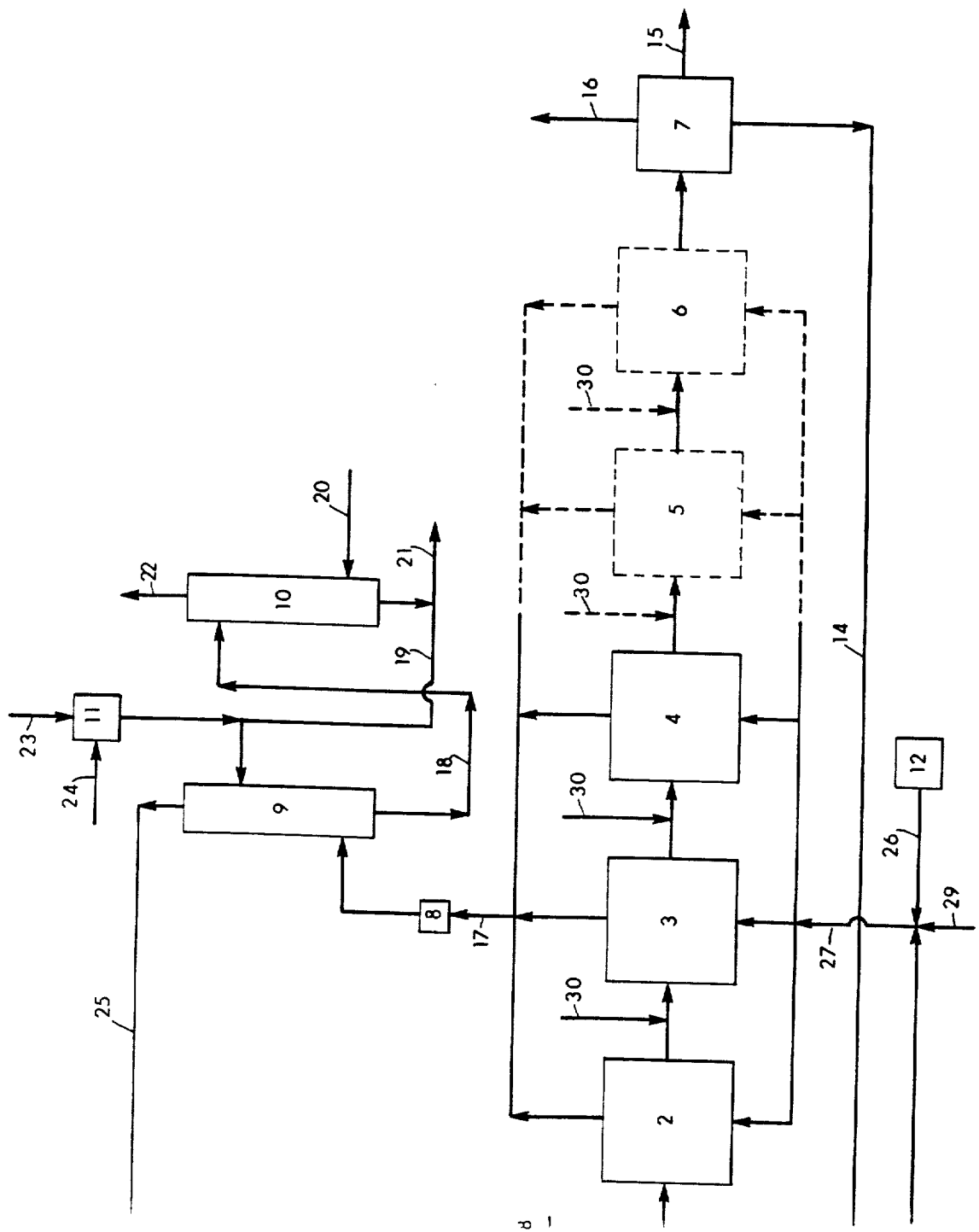

UNITED STATES PATENT AND TRADEMARK OFFICE
CERTIFICATE OF CORRECTION

PATENT NO. : 5,232,596

DATED : August 3, 1993

INVENTOR(S) : Frank J. Castaldi

It is certified that error appears in the above-identified patent and that said Letters Patent is hereby corrected as shown below:

Column 10, line 8 of the text: "z" should be "2".

Column 10, line 11 of the text: "z" should be "2".

Column 17, line 8 of the text: capital "O" of the word "of" should be lower case.

Table III: the word "1,1-Dichloroethane" (first occurrence) should be "1-1,Dichloroethene".

Table IV: "51" should be "5.1".

Column 25, line 11 Of the text: the word "organic-contaminated" should read "organics-contaminated".

Signed and Sealed this

Twenty-fifth Day of February, 1997

Attest:

BRUCE LEHMAN

*Attesting Officer*     *Commissioner of Patents and Trademarks*